(12) United States Patent
Yie et al.

(10) Patent No.: US 8,759,596 B2
(45) Date of Patent: Jun. 24, 2014

(54) LIQUID FUEL PRODUCTION PROCESS FROM CELLULOSIC BIOMASS AND COAL

(75) Inventors: Hongping Yie, Anhui (CN); Meg M. Sun, San Diego, CA (US); Zuolin Zhu, San Diego, CA (US)

(73) Assignee: China Fuel (Huaibei) Bioenergy Technology Development Co., Ltd, Anhui (CN)

( * ) Notice: Subject to any disclaimer, the term of this patent is extended or adjusted under 35 U.S.C. 154(b) by 1284 days.

(21) Appl. No.: 12/527,357

(22) PCT Filed: Apr. 6, 2007

(86) PCT No.: PCT/CN2007/001117
§ 371 (c)(1),
(2), (4) Date: Mar. 15, 2010

(87) PCT Pub. No.: WO2008/101370
PCT Pub. Date: Aug. 28, 2008

(65) Prior Publication Data
US 2010/0186291 A1    Jul. 29, 2010

(30) Foreign Application Priority Data
Feb. 16, 2007  (CN) .......................... 2007 1 0084896

(51) Int. Cl.
*C10L 1/182*    (2006.01)
(52) U.S. Cl.
USPC ................. 585/240; 44/436; 44/451; 44/452; 44/605; 44/606; 518/714

(58) Field of Classification Search
USPC ............. 44/436, 451–452, 605–606; 518/714
See application file for complete search history.

(56) References Cited

U.S. PATENT DOCUMENTS

| 4,882,360 A | 11/1989 | Stevens |
| 7,500,997 B2 * | 3/2009 | Norbeck et al. ............. 48/127.7 |

FOREIGN PATENT DOCUMENTS

| CN | 1631527 A | 6/2005 |
| CN | 1654313 A | 8/2005 |
| CN | 1230498 C | 12/2005 |
| CN | 1865408 A | 11/2006 |
| RU | 2241904 C1 | 12/2004 |
| WO | 2006/123158 A2 | 11/2006 |

* cited by examiner

*Primary Examiner* — Brian McCaig
(74) *Attorney, Agent, or Firm* — Hamre, Schumann, Mueller & Larson, P.C.

(57) ABSTRACT

A liquid fuel production process from Cellulosic biomass and coal comprises providing a mixture of Cellulosic biomass and coal, subjecting the mixture to gasification to obtain synthesis gas and converting the synthesis gas to a liquid fuel under the presence of catalyst. The catalyst includes molybdenum sulfide, alkali metal compound and a component activating the C—H bond in alkanes product, wherein the alkali metal compound is selected from the group of salts of Li, Na, K, Rb and Cs, the component activating the C—H bond in alkanes product is selected from Mo, V, Os, Re, Ir, Pt, Pd, Co, Rh, Ni and their mixture. Additionally, co-gasification of Cellulosic biomass and coal can reduce the ash fusion temperature of coal.

17 Claims, No Drawings

LIQUID FUEL PRODUCTION PROCESS FROM CELLULOSIC BIOMASS AND COAL

TECHNICAL FIELD

The present invention relates to a novel process for producing liquid fuel by using Cellulosic biomass as the raw material, more particularly to a process which comprises producing synthesis gas by co-gasifying Cellulosic biomass and coal, followed by producing liquid fuel from the synthesis gas.

BACKGROUND ART

Since the beginning of this century, the supply of oil energy sources has arrived at its peaks. According to the data specified in the "BP Statistical Review of the World Energy 2005", based on the present exploitation rate, the reserves of oil in the world can be further sustained for a little more than 40 years, and the reserves of natural gas and coal can be sustained for about 67 years and 164 years, respectively. It can be expected that the liquid fuel can not be replaced during quite a long period based on the current technology of the human society. As can be seen, mankind has to face the most vital turning point in history. Meanwhile, the global warming is regarded as the prime cause of various synoptic disasters around the world in recent years and may be attributed largely to the greenhouse gas, i.e. carbon dioxide, most of which originates from fossil energy sources. Therefore, new renewable energy sources must be developed and utilized so as to ensure the continuing existence and sustainable development of human beings.

Although the process of producing biomass derived ethanol fuel by fermentation is being widely spread in the field of liquid fuel, the actual application thereof is limited by the two factors as follows: (1) the process of producing ethanol fuel from starch will consume the food for mankind, (2) the cost of the process of producing ethanol fuel from cellulose is far higher than that derived from starch. It is true that we have developed a technology for rapid pretreatment of Cellulosic biomass at room temperature under atmospheric pressure and a corresponding novel production process (PCT/CN2006/000120), the cost of producing ethanol fuel through fermentation of Cellulosic biomass is thus expected to be substantially decreased. However, since such process is limited by the current technology level, the cost of ethanol fuel produced through fermentation of Cellulosic biomass can only be lowered to a level comparable to that of starch derived ethanol fuel.

The process of producing liquid fuel from coal can be the leading trend since the reserves of coal is much higher than that of oil. Currently, there are two coal liquefaction processes for producing liquid fuel, namely, coal direct liquefaction and indirect liquefaction. However, the production conditions used in the process of producing liquid fuel by direct coal liquefaction is too rigor and only limited types of coal can be used therein. The process of producing methanol by indirect coal liquefaction is usually preferred because of the following reason: the production procedures currently used for preparing methanol fuel from synthesis gas is relatively well developed, and the conditions for coal gasification is much mild than those used for the direct coal liquefaction; the cost for producing methanol through indirect coal liquefaction is less than one third of that for producing ethanol fuel; the combustion value per unit weight of methanol fuel is 76.5% of that of the ethanol fuel; and the corrosive to engine caused by methanol can be readily resolved. For the above reasons, the development of methanol fuel will be of great competitiveness. Furthermore, we have just developed a process for producing saturated alkane (diesel oil and gasoline) from Cellulosic biomass, and there is still a long way to go before the process can be applied in the commercial scale. As can be seen, the methanol, ethanol, and the derivates thereof derived from Cellulosic biomass, coal and natural gas will necessarily become the dominant liquid fuel in the near future.

The process currently used for producing methanol through indirect coal liquefaction mainly comprises two steps as follows: in the first step, the coal is gasified to produce synthesis gas, and in the second step, the synthesis gas is converted into methanol in the presence of catalyst. Relatively developed coal gasification process mainly comprises the gasification of solid coal powder feedstock and the gasification of aqueous coal slurry feedstock. The process of gasification of aqueous coal slurry feedstock is more homogeneous and highly reliable, so the yield of synthesis can be more readily enhanced by carrying out the gasification under high pressure. Therefore, the process of the gasification of aqueous coal slurry feedstock is generally adopted, while the gasification of solid coal powder feedstock is stilled operated by some manufactures. However, the process of producing methanol through indirect coal liquefaction still possesses the following drawbacks that need to be improved:

First of all, since the coal is generally rich in carbon but lack of hydrogen, the composition of the synthesis gas derived from most types of coal is far lower than the ratio required for producing methanol (hydrogen:carbon monoxide=2:1). The methods previously used for solving above problem comprises: (1) installing a separate production line for generating hydrogen from coal so as to supplement the hydrogen; (2) installing a separate converter in the gasification process for converting carbon monoxide into hydrogen (by reacting carbon monoxide and water to produce carbon dioxide and hydrogen) so as to supplement. However, both of the above methods still include the limitations of increasing the cost and the complexity of the process, and consumption of water and coal. It is well known that the short supply of water will be more and more severe in the future. The difficulties in gasification is even more severe for some types of coal, such as the coal produced from the Eastern China, which not only are rich in carbon and lack of hydrogen but also comprise excessive ash content with high ash fusion temperature (1500° C. or even higher), etc.

Secondly, in addition to the above drawbacks, many types of coal will bring about the problem of extremely high energy consumption when used for producing methanol through indirect coal liquefaction. In the process of coal gasification, the liquid slag-tapping is generally preferred, and the liquid slag-tapping from the lower-part is more preferred for the sake of easiness in operation. The optimal operation temperature for the liquid slag-tapping furnace is usually 30-50° C. higher than the ash fusion temperature, that is, the optimal operation temperature of coal gasifying for the slag-tapping furnace is usually at least about 1550° C. when the ash fusion temperature is higher than 1500° C. or more. When carrying out the coal gasification reaction under such a high temperature, the energy consumption as well as the rate of the reaction between hydrogen and carbon to produce methanol and ethanol will be rapidly increased, and the virtual specific yield of gas will decrease. Furthermore, if the operation temperature is higher than 1400° C., the fusion corrosion rate of firebrick will double every the temperature increasing 20° C. When the operation temperature is 1550° C., the firebrick will have to be replaced more frequently because of its high fusion corrosion rate, which will severely enhance the cost of production.

The conventional technical solution aimed to solve the problem is to incorporate calcium oxide (calcium carbonate), ferric oxide, or magnesium oxide (magnesium carbonate), etc. therein to decrease the ash fusion temperature. However, since the amount of calcium oxide incorporated therein is generally 20-25% based on the total amount of the ash, above solution will substantially increase the output of ash. Meanwhile, the cost will be excessively high by using sodium carbonate or potassium carbonate. Every time the ash content is increased by 1%, the consumption of oxygen and coal will increase by about 0.8% and 1.5%, respectively. Therefore, the production cost will be further enhanced and the specific yield will be further lowered. Besides, the incorporation of fluxing agent of calcium oxide will result in black water treatment and severe fouling of the thermal-exchange system, rendering great increase of the total production cost.

In additional to synthesizing methanol liquid fuel, the synthesis gas can also be used for producing other liquid fuel such as ethanol. The chemical mechanism of producing ethanol from synthesis gas is similar with the mechanism of producing methanol. Accordingly, the catalyst used for producing methanol can be used as a basis and modified to obtain the catalyst used for producing ethanol. Besides, the reaction equipments used for the process of producing ethanol may be the same with the reaction equipments used for the methanol with tiny variation, which is mainly because the process of producing ethanol will emits more heat (about 2.5 times of the process of producing methanol), thus the reaction vessel has to be modified so that the heat can be dissipated rapidly.

In addition to the eager need for improving the process of producing liquid fuel through coal gasification, the process of producing methanol through direct Cellulosic biomass gasification also encounters many issues. Firstly, the Cellulosic biomass is of low density, rendering an excessively low efficiency of the gasification furnace and high specific cost of the product; secondly, the Cellulosic biomass is rich in hydrogen and lack of carbon, rendering the excessive hydrogen in the synthesis gas can not be effectively used for the synthesis of methanol, and consequently leading to high specific cost of the production.

SUMMARY OF THE INVENTION

One object of the present invention is to provide a highly effective novel process of producing synthesis gas and liquid fuel by using a combination of coal and Cellulosic biomass. The novel process effectively takes advantage of coal which is rich in carbon and lack of hydrogen as well as the Cellulosic biomass which is rich in hydrogen and lack of carbon, so that synthesis gas having composition approaching the optimal ratio for producing alcohol products, such as methanol and ethanol can be obtained by an one-step gasification.

Another object of the present invention is to provide a process of producing liquid fuel from Cellulosic biomass with high conversion, without biomass pretreatment and the separation of the components.

In one aspect of the present invention, a process for producing fuel from the Cellulosic biomass is provided, wherein the process comprises the following steps:
the first step, a mixture of cellulose and coal is provided; and
the second step, the mixture of the first step is gasified to produce a synthesis gas fuel.

In one particular embodiment of the invention, the process of producing fuel from the Cellulosic biomass of the present invention comprises the following steps: the first step, a mixture of cellulose and coal at a proper ratio is provided, wherein the "proper ratio" means that said mixture will exhibit lower ash fusion temperature and the combustion value meeting the requirement on the efficiency of the gasification furnace; the second step, the mixture of the first step is gasified to produce a synthesis gas, wherein the sulfur content in the synthesis gas is notably lower than that of the synthesis gas produced by solely using coal. The synthesis gas of the present invention can be solely used as fuel, namely synthesis gas fuel.

Preferably, the content of the Cellulosic biomass in the first step is 1-99 wt. %, based on the total weight of the mixture; and/or
the particle size of the mixture of the first step is 25-500 mesh, and/or
the mixture of the first step comprises 25-50 wt. % of water, based on the weight of the mixture, to obtain a aqueous slurry; and/or
the temperature of the mixture in the first step is between 200° C. and 500° C.; and/or
the pressure of the mixture in the first step is between 5 and 60 atm.

Preferably, in the second step, the gasification is carried out in the present of a oxygen-containing gas, wherein the oxygen-containing gas is selected from air, pure oxygen or a combination thereof, and the oxygen content of the oxygen-containing gas is 0.8-1.5 molar equivalence on the basis of the carbon content in the coal and Cellulosic biomass; and/or
the gasification temperature of the second step is between 1000° C. and 1800° C.

Furthermore, the process comprises the following step: the third step, the synthesis gas fuel produced in the second step will be converted into liquid fuel.

Preferably, the liquid fuel of the third step is methanol and/or ethanol; and/or
the conversion of the third step is operated in the present of catalyst; and/or
the synthesis gas fuel of the third step comprises hydrogen and carbon monoxide, wherein the molar ratio of the hydrogen to carbon monoxide is between 1:10 and 10:1.

Preferably, said catalyst is a catalytic system comprising molybdenum sulfide and a component for activating the C—H bond in the alkane product; and/or
The catalyst is calcined under the ultrasonic.

Preferably, the component for activating the C—H bond in the alkane product is selected from Mo, V, Os, Re, Ir, Pt, Pd, Co, Rh, Ni and the combination thereof.

Preferably, the catalytic system consists of Mo—S-M-L;
wherein, M is the component for activating the C—H bond in the alkane product;
L is a alkali metal compound used as the activity enhancer in the catalytic system;
wherein, the molar ratio is Mo(100%)-S(175%-200%)-M(10%-100%)-L(150%-190%).

Preferably, M is selected from Mo, V, Os, Re, Ir, Pt, Pd, Co, Rh, Ni, or the combination thereof; and/or
L is selected from the salts of Li, Na, K, Rb, Cs; and/or
the catalytic system is prepared by the deposition method; and/or
the catalytic system is supported on a carrier material.

In another aspect of the present invention, there is provided a use of the Cellulosic biomass, and specifically, co-gasifying the Cellulosic biomass and coal so as to reduce the ash fusion temperature of the coal gasification.

BEST MODES FOR CARRYING OUT THE INVENTION

The present invention relates to a process of producing synthesis gas and liquid fuel through co-gasification of Cellulosic biomass and coal. The present invention can effectively lower the ash fusion temperature of coal, so that the coal with high ash fusion temperature can be used for producing liquid fuel through indirect process. In particular, when coal and Cellulosic biomass are co-gasified under specified ratio, the defects of them can be effectively eliminated, resulting in an improved process for producing methanol and ethanol with reduced cost.

In the production process of the present invention, by making use of the mixture of cellulose and coal, the ash fusion temperature and hence the optimal operation temperature of the coal gasification are both decreased, and the incorporation of the fluxing agent such as calcium oxide can also be avoided. Besides, the energy consumption during the coal gasification, the production of methane and ethane through the reaction between hydrogen and carbon in the system, as well as the fusion corrosion rate of the firebrick can all be decreased. Meanwhile, in the unique process, the yield of ash content as well as the consumptions of oxygen and coal and the cost can be reduced. The blackwater treatment and fouling in the thermal exchanging system can be alleviated, so that the total cost can be remarkably reduced. Furthermore, in the novel process, a large amount of Cellulosic biomass is used as starting materials, thus reducing the dependence on fossil energy resources and emission of the greenhouse gas carbon dioxide, which is advantageous to the environmental protection as well as living and development of mankind.

In the unique process, since the ash fusion temperature during the gasification is decreased, more types of coal, for example the coal having extremely high ash fusion temperature such as the coal from Eastern China, can be used as the starting material for coal gasification to produce synthesis gas, and subsequently used for the indirect coal liquefaction.

Besides, the synthesis gas produced by present invention exhibits favorable ratio of hydrogen to carbon monoxide. For example, the content of hydrogen may be 37-60 vol. %, based on the total volume of the synthesis gas.

The water content in the natural drying coal and Cellulosic biomass will meet the requirement of the process of the present invention.

Cellulosic biomass according to the invention is defined as biomass containing cellulose. The cellulose of the present invention includes, but not limited to polysaccharide celluloses and hemicelluloses. Biomass refers to residual substances rich in biomass energy after removing their edible parts. The biomass of the present invention includes, but not limited to the inedible parts of various crops, such as corn stalk, broomcorn stalk, wheat straw, soy stalk, cotton stalk, as well as other biomass including reed, bamboo, various hard and soft wood, weeds, etc. The natural drying biomass generally has a water content of less than 5%.

The coal of the present invention is not particularly limited, as long as the object of the present invention will not be hindered thereby. In common words, the process of the present invention is applicable to all kinds of coal. In particular, the coal used in the present invention may have a ash content of 5-30%, and the procedure is no longer limited by the ash fusion temperature of the coal.

Regarding the mixture of Cellulosic biomass and coal of the present invention, the amount of Cellulosic biomass shall be adjusted so that the solid substances charged into the gasification furnace has a combustion heat per unit of no less than 25 KJ/Kg. In particular, the content of Cellulosic biomass can be 1-99 wt. %, based on the total weight of the mixture. However, for different types of coal, the content of cellulose used for the gasification process is preferably between 5 wt. % and 25 wt. %, based on the total weight of the mixture, so that the gasification furnace can be operated more efficiently. All of the above amounts are calculated by weight.

The mixture is preferably comminuted. The coal and Cellulosic biomass can be co-comminuted or separately comminuted. The particle size of the comminuted substances is 25-500 mesh, more preferably 125-300 mesh.

The process of the present invention can be used in both the gasification of aqueous slurry feedstock and the gasification of solid powder feedstock.

When the coal and Cellulosic biomass are separately comminuted and charged to the gasification procedure as the form of aqueous slurry, the aqueous slurries of coal and Cellulosic biomass can be separately formulated and combined before they are charged into the gasification furnace. Alternatively, the coal aqueous slurry can be prepared first, into which the powder of Cellulosic biomass is added to get the slurry for gasification. The content of water in the aqueous slurry as prepared is generally 50 wt. %, based on the total weight of the aqueous slurry, preferably 40 wt. %, more preferably at least 25 wt. %, further preferably no less than 30 wt. %. Accordingly, the sum of the content of coal and Cellulosic biomass in the aqueous slurry is generally 75 wt. %, based on the total weight of the aqueous slurry, preferably 70 wt. %, more preferably at least 50 wt. %, further preferably no less than 55 wt. %. That is because in the slurry prepared from water, coal and Cellulosic biomass, when the content of water is excessively high, the gasification of water will consume too much energy, while when the content of water is too low, the slurry will have too high a viscosity to be pumped into the gasification furnace or sprayed by the nozzle.

The unique process of the present invention is further characterized in that a pre-heater can be disposed before the gasification furnace, so that the slurry of coal and Cellulosic biomass can be preheated to the temperature of 200-500° C. and the pressure of 5-60 atm. before it is charged into the gasification furnace. In such a process, the gasification can be carried out by using air rather than pure oxygen, thus rendering the cost of production.

During the gasification of the present invention, the mixture contacts with the oxygen-containing gas. Said oxygen-containing gas is not particularly limited, as long as the object of the present invention is not hindered thereby. For example, the air, pure oxygen, gas mixture of oxygen and inert gases, etc. are all usable. When air is used in the present invention, the content of oxygen is preferably 1.5 molar equivalence based on the carbon content in the mixture of the coal and Cellulosic biomass (e.g. slurry), or no less than 1.1 molar equivalence, wherein the content oxygen is calculated based on the oxygen contained in the air. When no pre-heater is disposed, the content of pure oxygen is usually 1.1 molar equivalence based on the carbon content in the mixture of the coal and Cellulosic biomass (e.g. slurry), or no less than 0.8 molar equivalence.

The temperature for gasification is not particularly limited in the present invention, as long as the object of the present invention is not hindered. The gasification temperature of the gasification furnace is generally between 1000° C. and 1800° C., preferably between 1100° C. and 1600° C., more preferably between 1300° C. and 1500° C.

In the present invention, the "synthesis gas fuel" refers to the gas fuel produced during the gasification, which can be used for the subsequent synthesis. For example, the synthesis gas fuel may comprises hydrogen and carbon monoxide, and can be used for preparing methanol and/or ethanol. In a particular example, the high temperature gas from the gasification furnace is cooled in a heat exchanger, and the recovered heat can be used for other procedures such as drying the Cellulosic biomass. The cooled gas undergoes the procedures of gas filter, water scrubber, oil scrubber and acid stripping, and then can be used as synthesis gas for preparing methanol and/or ethanol.

The present invention further provides a highly efficient process for producing ethanol comprising: converting all the organic carbon in the Cellulosic biomass, including cellulose, hemicellulose and lignose, into synthesis gas; and then the synthesis gas is converted into liquid fuel such as methanol and ethanol. In contrast, during the fermentation of monosaccaride, organic carbon will be consumed by the growth and living of the microzyme. For example, when hexose is used as the monosaccharide, one third of the organic carbons lost during the fermentation. When pentose is used as the monosaccaride (the pentose merely refers to xylose, and arabinose will be totally lost since it can not be fermented), sixty percent of the organic carbons are lost during the fermentation.

The liquid fuel of the present invention is not particularly limited, as long as it can be prepared from the synthesis gas obtained from the gasification of Cellulosic biomass and coal. For example, the liquid fuel can be C1-C4 alcohol, and a particular example thereof is methanol and/or ethanol.

Catalyst can be used in the conversion. Preferably, catalyst comprising molybdenum sulfide ($MoS_2$) as the main component is used for the preparation of ethanol since the system exhibits excellent sulfur-resistance. Since the synthesis gas prepared from coal generally comprises a lot of sulfur, if the Snam, Lurgi or IFP catalyst system is adopted, the synthesis gas shall be purified by severe desulfurization to a sulfur level of $10^{-9}$, rendering a substantially increased production cost. However, the molybdenum sulfide comes along with a severe shortcoming, i.e. a large amount of alkane products (such as methane, ethane, etc.) will be produced by the catalyst system during the process. Another key point of the present process resides in that the catalytic system comprises a component for activating the C—H bond in the alkane products. In the present invention, the component for activating the C—H bond in the alkane product includes, separately or in combination, molybdenum (Mo), vanadium (V), osmium (Os), rhenium (Re), iridium (Ir), platinum (Pt), palladium (Pd), cobalt (Co), rhodium (Rh), nickel (Ni), etc.

The catalytic system is preferably composed of Mo—S-M-L, wherein M is a component for activating the C—H bond in the alkane product and is selected from molybdenum (Mo), vanadium (V), osmium (Os), rhenium (Re), iridium (Ir), platinum (Pt), palladium (Pd), cobalt (Co), rhodium (Rh) and nickel (Ni); L is a alkali metal compound used as the activity enhancer for the catalytic system, wherein the alkali metal compound may be in various form, such as the salts (e.g. carbonate, halide, etc.) of lithium (Li), sodium (Na), potassium (K), rubidium (Rb) and cesium (Cs), etc., and the content thereof in the catalytic system is generally 0.1-10 wt. %, based on the alkali metal element.

The catalytic mechanism of the present invention is as follows:

The carbon monoxide is activated and hydrogenated, followed by the insertion of another carbon monoxide. The activation of C—H bond in the saturated alkane involves identical metal-activated intermediate, wherein M is the activating center of the catalyst system.

The activation of carbon monoxide:

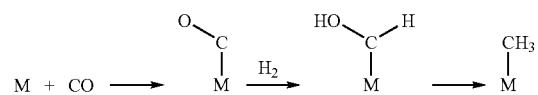

The activation of the C—H bond in the saturated alkane:

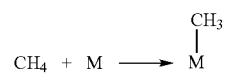

When both of the catalytic systems are cooperatively integrated, the formation of alkanes (methane, ethane, etc.) in the reaction will be reduced by the mechanism of insertion of carbon monoxide and the mechanism of activation of the C—H bond in the saturated alkanes, thus increasing the yield of ethanol and achieving the object of producing ethanol from the synthesis gas.

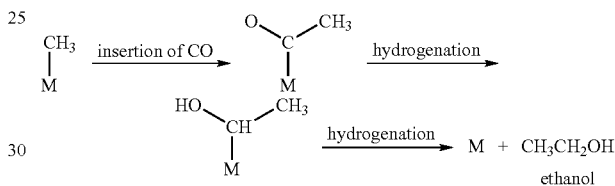

The method for preparing the catalyst of the present invention is not particularly limited, as long as the object of the present invention is not hindered. Generally, the molybdenum sulfide used in the catalyst is prepared by precipitation method by using ammonium molybdate as the starting material. The component M for activating the C—H bond in the alkane product can be in the form of elementary substance, salt (such as water soluble salt), oxide, sulfide and other forms. When the salt of component M for activating the C—H bond in the alkane product is a water soluble salt, such as palladium nitrate, iridium chloride, cobalt nitrate, rhodium nitrate, osmium chloride, etc., the catalyst system of Mo—S-M is usually prepared by co-precipitation. When the salt of component M for activating the C—H bond in the alkane product is a water insoluble salt, such as platinum oxide, molybdenum oxide, rhenium oxide, etc., the catalyst is usually prepared by directly co-grinding the solid oxide thereof along with the molybdenum sulfide prepared by precipitation to mix them uniformly. The content of the component for activating the C—H bond in the alkane in the catalytic system is generally 0.1-20.0 wt. %, based on the weight of elements, so that the molar ratio of Mo—S-M-L is Mo(100%)-S(175%-200%)-M(10%-100%)-L(150%-190%).

The catalyst of the present invention can be supported or unsupported. The unsupported catalyst is usually prepared by co-calcining the ammonium salt or potassium salt thereof to degradation. With regard to the supported catalyst, the support is usually selected from silica, alumina, clay such as Bentonite clay and activated carbon, wherein neutral silica, alumina and activated carbon is preferred, and the catalyst is prepared by impregnation or dry impregnation. In the dry impregnation, the solid prepared by precipitating or mixing-grinding is calcanied at 400-800° C., then ground to 140-200 mesh under the protection of inert gas, and at last is dispersed onto the support under vibration. In the impregnation method, the supported catalyst is prepared by loading the solutions of the activity enhancer and the molybdenum sulfide onto the support, followed by drying and calcination. During the procedure of impregnation, the activity enhancer of alkali metal is generally incorporated, followed by the component of molybdenum, and ultrasonic field is usually applied during the impregnation.

The catalyst is preferably calcinated under the ultrasonic field. The calcination temperature is preferably 400-800° C. and the calcination time is preferably 1-10 hours. The intensity of the ultrasonic is not particularly limited, as long as the object of the present invention will not be hindered thereby. In particularly, the catalyst is calcinated at 500° C. and ultrasonic intensity of 2 kW/2 kHz for 2 hour. The ratio between hydrogen and carbon monoxide of the synthesis gas in the synthesis reactor is 1:10 to 10:1, and the ratio of hydrogen to carbon monoxide favorable for synthesizing methanol and ethanol shall be approximately 2:1.

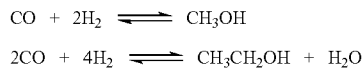

The temperature and pressure used for the process of converting the synthesis gas fuel to liquid fuel is not particularly limited, as long as the object of the present invention is not limited. The process can also be carried out according to the prior art.

The process for synthesizing and supporting the catalyst and the process for converting the synthesis gas as described above are just part of the synthesizing processes of the present invention. A person skilled in the art may, on the basis of the above examples, take advantage of various modified methods to prepare the catalyst of the present invention or promote the conversion of the synthesis gas. A person skilled in the art can also prepare the catalyst or liquid fuel of the present invention according to the existing common knowledge. The catalyst or liquid fuel as prepared can be further purified by various technical means of the prior art.

On the basis of the disclosure contained in the present invention, the other aspects of the present application are obvious to those skilled in the art.

Unless otherwise defined or stated, the meaning of the specific and scientific terminology used in the present invention is the same as those well known to the persons skilled in the art. Besides, any means or materials identical or corresponding to those specified can also be applied in the present invention.

The present invention is particularly illustrated by the specific examples as follows. In the following examples, the experimental methods in which the conditions are not particularly specified are carried out under conventional conditions or under the conditions as suggested by the manufacturers. Unless otherwise stated, the ratio and percentage are based on weight.

The following examples are intended to provide better understanding of the invention, by no means limiting the disclosure of the invention to those examples. The coal used in the examples has an ash content of 9-11% and an ash fusion temperature of 1490-1530° C., wherein the ash mainly comprises 50-57% silica and 30-37% alumina.

The gasification reactor is an experimental scale Texaco fluidized bed reactor. The solid weight of the feedstock is 800-1000 g/hour. The resulting gases being purified by standard methods, are analyzed by the gas chromatography (Hewlett Packard-5890-Series II) using standard gas as the standard. The synthesis of ethanol is carried out in an experimental scale Fischer-Tropsch tubular reactor loaded with catalyst to prepare the ethanol at 300° C., 68 atm, and the GHSV of the gas is 5400/hour.

EXAMPLE 1

The Gasification of Cellulosic Biomass and Coal

The gasification process is carried out at 1580° C. by separately using pure coal, coal containing 5% broomcorn stalk, coal containing 10% broomcorn stalk, coal containing 15% broomcorn stalk, coal containing 20% broomcorn stalk as the raw materials. Each groups of data are the average value of six experimental results. The compositions of the gases produced in the experiments are listed as follows.

| Composition (vol. %) | CO | $CO_2$ | $H_2$ | $CH_4$ | $H_2S$ | $N_2$ | Ar |
|---|---|---|---|---|---|---|---|
| pure coal | 46.4 | 12.0 | 33.0 | 8.0 | 0.2 | 0.3 | 0.1 |
| A. coal containing 5% broomcorn stalk | 45.1 | 8.9 | 37.5 | 8.0 | 0.1 | 0.3 | 0.1 |
| B. coal containing 10% broomcorn stalk | 41.9 | 8.1 | 41.5 | 8.0 | 0.1 | 0.3 | 0.1 |
| C. coal containing 15% broomcorn stalk | 39.7 | 7.1 | 44.7 | 8.0 | 0.1 | 0.3 | 0.1 |
| D. coal containing 20% broomcorn stalk | 36.5 | 5.0 | 50.5 | 7.5 | 0.1 | 0.3 | 0.1 |

As illustrated, when broomcorn stalk and coal are co-gasified, the volume percentage of the hydrogen contained in the gas composition is notably increased and that of CO and $CO_2$ are notably decreased. Meanwhile the amount of hydrogen sulfide is decreased accordingly.

At the end of each groups of six experiments, the resulting ash is separately collected and measured for their ash fusion temperature, and the results are listed as follows.

| Reaction group | pure coal | A | B | C | D |
|---|---|---|---|---|---|
| ash fusion temperature (° C.) | 1520 ± 11 | 1410 ± 8 | 1303 ± 7 | 1227 ± 9 | 1158 ± 5 |

As illustrated, when broomcorn stalk and coal are co-gasified, the ash fusion temperature thereof is substantially decreased. Specifically, when the content of broomcorn stalk is 10 wt. % of the total weight of the solid used for gasification, the ash fusion temperature is about 1300° C., which is substantially lower than that resulted when coal is solely used.

EXAMPLE 2

The Gasification of Coal Containing 10% Broomcorn Stalk

In Example 2, the procedure of Example 1 is followed, with the exception that the gasification is carried out at 1350° C. by using the coal containing 10% broomcorn stalk. The resulting gases are analyzed by gas chromatography. Each groups of data are the average value of six experimental results. The compositions of the gases produced in the experiments are listed as follows.

| Composition (vol. %) | CO | CO$_2$ | H$_2$ | CH$_4$ | H$_2$S | N$_2$ | Ar |
|---|---|---|---|---|---|---|---|
| B. coal containing 10% broomcorn stalk | 43.2 | 7.9 | 46.4 | 2.0 | 0.1 | 0.3 | 0.1 |

As illustrated, as compared with the gasification of coal containing 10% broomcorn stalk at 1580° C., the gasification of example 2 exhibits a notable decrease of the yield of methane and consequently an increase of both the contents of CO and H$_2$.

EXAMPLE 3

The Preparation of Catalyst for Producing Ethanol

The catalyst containing single component for activating the C—H bond:
60 g ammonium molybdate ((NH$_4$)$_2$MoO$_4$) is dissolved in 420 mL of aqueous solution of ammonium sulfide under stirring, and the resulting matter is stirred at 60° C. for 60 minutes (solution A). Solution B is prepared by dissolving 54 g palladium nitrate in 760 mL deionized water. The solutions A and B are simultaneously added dropwise into 400 mL 30 wt. % aqueous solution of acetic acid over 90 minutes, during which the temperature of the mixed liquid is kept at 50° C. The solid mixture thus prepared is further stirred at 50° C. for 90 minutes, and filtrated under vacuum to produce a solid product which is dried at room temperature for one day. The dried solid is equally divided into two parts, namely CA and CB. CA is calcinated at 500° C. for 2 hours and ultrasonic field intensity of 2 kW/20 kHz under the protection of nitrogen, while CB is calcinated at the same conditions but in the absence the ultrasonic field.
γ-alumina is impregnated in the water and the pH value of the resulting mixture is adjusted to 10 with saturated aqueous solution of potassium carbonate. After stable state has been established, the γ-alumina containing potassium carbonate is filtrated and dried at 150° C. for 4 hours.
5 g solid CA and 10 g γ-alumina containing potassium carbonate are separately weighed and homogeneously ground and mixed to produce the catalyst CAU; 5 g solid CB is similarly treated to produce the catalyst CBNU.
The catalyst containing two components for activating the C—H bond:
60 g ammonium molybdate is dissolved in 420 mL of aqueous solution of ammonium sulfide under stirring, and the resulting mixture is stirred at 60° C. for 60 minutes (solution A). Solution B is prepared by dissolving 27 g palladium nitrate in 380 mL deionized water. Solution C is prepared by dissolving 21 g cobalt acetate in 380 mL deionized water. The solutions A, B and C are simultaneously added dropwise into 400 mL 30 wt. % aqueous solution of acetic acid over 90 minutes, during which the temperature of the mixed liquid is kept at 50° C. The solid mixture thus prepared is further stirred at 50° C. for 90 minutes, and filtrated under vacuum to produce a solid product which is dried at room temperature for one day. The dried solid is equally divided into two parts, wherein MCA is the one calcinated at 500° C. for 2 hours and ultrasonic field intensity of 2 kW/20 kHz under the protection of nitrogen, while MCB is the one calcinated at the same conditions but in the absence the ultrasonic field. γ-alumina is impregnated in the water and the pH value of the resulting mixture is adjusted to 10 with saturated aqueous solution of potassium carbonate. After stable state has been established, the γ-alumina containing potassium carbonate is filtrated and dried at 150° C. for 4 hours.
5 g solid MCA and 10 g γ-alumina containing potassium carbonate are separately weighed and homogeneously ground and mixed to produce the catalyst MCAU; 5 g solid MCB is similarly treated to produce the catalyst MCBNU.

EXAMPLE 4

Comparison of the Catalytic Performances of Catalyst

The catalytic performances of above catalysts in the production of ethanol from synthesis gas is analyzed under the following conditions for comparison: the reaction temperature=300° C., the pressure=68 atm, GHSV=5400/hour, etc. The composition of product is determined by GC-MS and each groups of data are the average value of six experimental results. The compositions of the products produced in the experiments are listed as follows.

| Catalyst | methanol (%) | ethanol (%) | alkane (%) |
|---|---|---|---|
| CAU | 19 | 78 | 3 |
| CBNU | 25 | 70 | 6 |
| MCAU | 21 | 76 | 3 |
| MCBNU | 24 | 71 | 5 |

As illustrated, all the catalysts will exhibit favorable results, and the catalysts calcinated in the present of ultrasonic field (CAU and MCAU) will increase the amount of ethanol. There is no significant difference between the results obtained by the Mo—S—Pd—K system and Mo—S—Pd—Co—K system.

As compared with the catalyst system of the prior art, the catalyst system of the present invention is far better than those presently existing catalyst systems without the components for activating the C—H bond as to the selectivity of ethanol, ethanol:methanol≥1:3 (e.g. ethanol:methanol<1 when using the catalyst system of IFP, France), since the applicant has taken consideration of the concept of activating the C—H bond for the first time when developing the catalyst. The manufacturing process of the present invention can be specifically used for producing ethanol so as to significantly decrease the production cost of ethanol. (That is because the inventive system comprises low content of the byproduct methanol, which can be separated and recycled into the reactor to be converted into ethanol.)

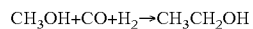

$$CH_3OH+CO+H_2 \rightarrow CH_3CH_2OH$$

The invention claimed is:
1. A process of producing fuel from a cellulosic biomass, comprising:
 a first step of providing a mixture of cellulosic biomass and coal;
 a second step of gasifying the mixture of the first step to produce a synthesis gas fuel; and
 a third step of converting the synthesis gas fuel produced in the second step into a liquid fuel in the presence of a catalyst,
 wherein the catalyst is calcinated in the presence of an ultrasonic field and comprises molybdenum sulfide and a component for activating a C—H bond in an alkane product.
2. The process according to claim 1, wherein
 the content of the cellulosic biomass in the first step is 1-99 wt. %, based on the total weight of the mixture.

3. The process according to claim 1, wherein
in the second step, the gasification is carried out in the presence of an oxygen-containing gas, the oxygen-containing gas is selected from air, pure oxygen and a combination thereof, and the oxygen content in the oxygen-containing gas is 0.8-1.5 molar equivalence on the basis of the carbon content in the coal and the cellulosic biomass.

4. The process according to claim 1, wherein,
the liquid fuel of the third step is methanol and/or ethanol.

5. The process according to claim 1, wherein,
the component for activating the C—H bond in the alkane product is at least one selected from the group consisting of Mo, V, Os, Re, Ir, Pt, Pd, Co, Rh, and Ni.

6. The process according to claim 1, wherein
the catalyst has the following formula (1)

Mo—S-M-L    (1);

where M is the component for activating the C—H bond in the alkane product;
L is an alkali metal compound used as an activity enhancer of the catalyst; and
a molar ratio of the formula (1) is Mo(100%)-S(175%-200%)-M(10%-100%)-L(150%-190%).

7. The process according to claim 6, wherein
M is at least one selected from the group consisting of Mo, V, Os, Re, Ir, Pt, Pd, Co, Rh, and Ni.

8. The process according claim 6, wherein L is at least one selected from the group consisting of a salt of Li, a salt of Na, a salt of K, a salt of Rb, and a salt of Cs.

9. The process according claim 6, wherein the catalyst is prepared by a precipitation method.

10. The process according claim 6, wherein the catalyst is supported on a carrier material.

11. The process according claim 1, wherein a particle size of the mixture of the first step is 25-500 mesh.

12. The process according claim 1, wherein the mixture of the first step is an aqueous slurry that comprises 25-50 wt. % of water based on the weight of the mixture.

13. The process according claim 1, wherein a temperature of the mixture in the first step is 200-500° C.

14. The process according claim 1, wherein a pressure of the mixture in the first step is 5-60 atm.

15. The process according claim 1, wherein the synthesis gas fuel of the third step comprises hydrogen and carbon monoxide, and wherein a molar ratio of the hydrogen to carbon monoxide is between 1:10 and 10:1.

16. The process of claim 1, wherein a gasification temperature of the second step is 1000-1800° C.

17. The process of claim 1, wherein the catalyst is calcinated at an ultrasonic field intensity of 2 kW/20 kHz.

* * * * *